United States Patent [19]

Manimaran et al.

[11] Patent Number: 5,302,751

[45] Date of Patent: Apr. 12, 1994

[54] PROFEN RESOLUTION

[75] Inventors: Thanikavelu Manimaran; Alicia A. Potter, both of Baton Rouge, La.

[73] Assignee: Ethyl Corporation, Richmond, Va.

[21] Appl. No.: 823,367

[22] Filed: Jan. 21, 1992

[51] Int. Cl.⁵ .................. C07B 57/00; C07D 307/02; C07C 67/60

[52] U.S. Cl. .................. 562/401; 548/572; 549/79; 549/499; 558/414; 560/17; 560/21; 560/22; 560/43; 560/52; 560/55; 560/56; 560/61; 560/100; 560/102; 560/105; 562/402

[58] Field of Search ............... 562/401, 402; 560/17, 560/21, 22, 43, 52, 55, 56, 61, 100, 102, 105; 549/499, 79; 548/572; 558/414

[56] References Cited

U.S. PATENT DOCUMENTS

| | | | |
|---|---|---|---|
| 4,723,033 | 2/1988 | Erickson | 560/56 |
| 4,983,765 | 1/1991 | Lukas et al. | 562/401 |
| 4,994,604 | 2/1991 | Tung et al. | 562/401 |
| 5,015,764 | 5/1991 | Manimaran et al. | 562/401 |

OTHER PUBLICATIONS

Jaques et al., *Enantiomers, Racemates and Resolutions,* pp. 193–196, John Wiley and Sons, Inc., New York (1981).

Sheldon, *Chemistry & Industry,* Apr. 2, 1990, pp. 212–219.

*Primary Examiner*—José G. Dees
*Assistant Examiner*—Vera C. Clarke
*Attorney, Agent, or Firm*—Richard J. Hammond

[57] ABSTRACT

A process is disclosed that is useful for separating the enantiomers of a racemic mixture of an aliphatic carboxylic acid having the formula

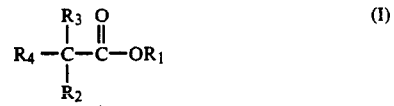

where $R_1$ is hydrogen or alkyl, $R_2$, $R_3$ and $R_4$ are independently different and are hydrogen, alkyl, cycloalkyl, alkenyl, alkynyl, phenyl, substituted phenyl, naphthyl, substituted naphthyl, heteroaryl, substituted heteroaryl, haloalkyl, alkoxyalkyl, alkylthioalkyl, phenylalkyl, substituted phenylalkyl, heteroalkylalkyl, substituted heteroalkylalkyl or cycloalkylalkyl.

The process comprises forming a conglomerate salt by reacting the racemic mixture with a base, the conglomerate salt being a mixture of the enantiomeric salts and having the following properties:

i) the infrared spectrum of each of the enantiomeric salts, individually, and of the racemate salt are superposable;

ii) the melting point of each of the enantiomeric salts, individually, is greater than the melting point of the racemate salt; and iii) the solubility of each of the enantiomeric salts, individually, is less than the solubility of the racemate salt in the same solvent.

The enantiomeric salts are readily separable from the racemic mixture.

13 Claims, No Drawings

PROFEN RESOLUTION

FIELD OF INVENTION

This invention relates to a process for obtaining a pure enantiomer of an aromatic substituted aliphatic carboxylic acid from a mixture of enantiomers, either racemic or enriched with the desired enantiomer.

BACKGROUND OF INVENTION

Asymmetric synthesis and the resolution of racemates constitute the methods for industrial preparation of pure enantiomers. Methods for such resolution include: direct preferential crystallization, crystallization of the diastereomeric salts, and kinetic resolution.

Also referred to as resolution by entrainment, preferential crystallization is economically more attractive because resolution is achieved without using any expensive optically active substance. Hence, this method is widely used on an industrial scale, for example, in the manufacture of α-methyl-L-dopa and chloramphenicol. See *Enantiomers, Racemates, and Resolutions*, Jacques, J.; Collet, A.; Wilen, S.H., J. Wiley & Sons, New York, 1981; Jacques, J.; Leclercq, M.; Brienne, M.J., *Tetrahedron*, 1981, 37, 1727–1733; and U.S. Pat. No. 4,865,770. It is technically feasible only with racemates which are so-called conglomerates and consist of mechanical mixtures of crystals of the two enantiomers. Unfortunately, only less than 20% of all racemates are conglomerates. The rest are true racemic compounds which cannot be separated by preferential crystallization (i.e., by seeding a supersaturated solution of racemic mixture with the crystals of one enantiomer). A conglomerate exhibits a minimum melting point for the racemic mixture while a racemic compound generally shows a maximum melting point. The success of preferential crystallization depends on the fact that the solubility of pure enantiomer is less than the solubility of the racemic mixture.

OBJECTS OF THE INVENTION

Ibuprofen is a racemic compound and hence cannot be resolved by preferential crystallization. Suprisingly, it has been found, and it is the object of the present invention, that achiral and racemic amine salts of racemic ibuprofen can be resolved with no use of optically active substances by means of direct crystallization method.

Enantiomers of conglomerates can be resolved by direct crystallization. Accordingly, it is an object of the present invention to prepare salts of 2-(4-isobutylphenyl)propionic acid that are conglomerates.

It is a further object of the present invention to provide a process for separation of the enantiomers of conglomerate salts of 2-(4-isobutylphenyl)propionic acid.

It is a further object of the present invention to provide a process for obtaining a substantially pure enantiomer of ibuprofen.

It is another object of the present invention to obtain such substantially pure enantiomer from compositions of enantiomerically enriched racemic ibuprofen.

PREFERRED EMBODIMENTS OF THE INVENTION

In the above definitions and the present specification, alkyl means straight or branched chain alkyl having 1 to 20 carbon atoms, and includes, for example, methyl, ethyl, propyl, isopropyl, butyl, isobutyl, secondary butyl, tertiary butyl, pentyl, isopentyl, neopentyl, hexyl, heptyl, octyl, 2-ethylhexyl, 1,1,3,3-tetramethylbutyl, nonyl, decyl, dodecyl, tetradecyl, hexadecyl, octadecyl and eicosyl.

Cycloalkyl means cyclic alkyl having 3 to 7 carbon atoms, and includes cyclopropyl, cyclobutyl, cyclopentyl, cyclohexyl and cycloheptyl.

Alkenyl means straight or branched chain alkenyl having 2 to 8 carbon atoms, and includes, for example, vinyl, 1-propenyl, allyl, isopropenyl, 2-butenyl, 1,2-butanedienyl, 2-pentenyl, 2-hexenyl and octenyl.

Alkynyl means straight or branched chain alkynyl having 2 to 8 carbon atoms, and includes, for example, ethylnyl, 2-propynyl, butynyl, pentynyl, hexynyl, heptynyl and octynyl.

Substituted phenyl and substituted naphthyl means phenyl or naphthyl substituted by at least one substituent selected from the group consisting of halogen (chlorine, bromine, fluorine or iodine), amino, nitro, hydroxy, alkyl, alkoxy which means straight or branched chain alkoxy having 1 to 10 carbon atoms, and includes, for example, methoxy, ethoxy, propoxy, isopropoxy, butoxy, isobutoxy, secondary butoxy, tertiary butoxy, pentyloxy, isopentyloxy, hexyloxy, heptyloxy, octyloxy, nonyloxy and decyloxy, haloalkyl which means straight or branched chain alkyl having 1 to 8 carbon atoms which is substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-trifluoroethyl, 2,3,3-trifluoropropyl, 1,1,2,2-tetrafluoroethyl and 2,2,3,3-tetrafluoropropyl.

Heteroaryl means 5 to 10 membered mono- or fused-heteroaromatic ring which has at least one heteroatom selected from the group consisting of nitrogen, oxygen and sulfur, and includes, for example, 2-furyl, 3-furyl, 2-thienyl, 3-thienyl, 2-pyridyl, 3-pyridyl, 4-pyridyl, pyrazolyl, imidazolyl, pyrimidinyl, pyridazinyl, pyrazinyl, benzimidazolyl, quinolyl, oxazolyl, thiazolyl and indolyl.

Substituted heteroaryl means 5 to 10 membered mono- or fused-heteroaromatic ring which has at least one heteroatom selected from the group consisting of nitrogen, oxygen and sulfur and which is substituted by at least one substituent selected from the group consisting of halogen, amino, nitro, hydroxy, alkyl, alkoxy and haloalkyl on the above-mentioned heteroaromatic nucleus.

Haloalkyl means straight or branched chain alkyl having 1 to 10 carbon atoms which is substituted with at least one halogen as mentioned above.

Alkoxyalkyl means that the alkoxy moiety and the alkyl moiety each are straight or branched chain ones having 1 to 8 carbon atoms, and includes, for example, methoxymethyl, ethoxymethyl, propoxymethyl, isopropoxymethyl, butoxymethyl, isobutoxymethyl, tertiary butoxymethyl, pentyloxymethyl, hexyloxymethyl, heptyloxymethyl, octyloxymethyl, 2-methoxyethyl, 2-ethoxyethyl, 2-propoxyethyl, 2-butoxyethyl, 2-hexyloxyethyl, 2-octyloxyethyl, 3-methoxypropyl, 3-ethoxypropyl, 3-propoxypropyl, 3-butoxypropyl, 3-hexyloxypropyl, 3-octyloxypropyl, 4-methoxybutyl, 4-ethoxybutyl, 4-propoxybutyl, 4-butoxybutyl, 4-hexyloxybutyl, 4-octyloxybutyl, 5-methoxypentyl, 5-ethoxypentyl, 5-propoxypentyl, 5-butoxypentyl, 5-pentyloxypentyl, 5-hexyloxypentyl, 5-octyloxypentyl, 6-methoxyhexyl, 6-ethoxyhexyl, 6-propoxyhexyl, 6-butoxyhexyl, 6-pentyloxyhexyl, 6-hexyloxyhexyl, 6-octyloxyhexyl, 8-methoxyoctyl, 8-ethoxyoctyl, 8-butoxyoctyl, 8-hexyloxyoctyl and 8-octyloxyoctyl.

Alkylthioalkyl means that the alkylthio moiety and the alkyl moiety each are straight or branched chain ones having 1 to 8 carbon atoms, and includes, for example, methylthiomethyl, ethylthiomethyl, propylthiomethyl, isopropylthiomethyl, butylthiomethyl, isobutylthiomethyl, tertiary butylthiomethyl, pentylthiomethyl, hexylthiomethyl, octylthiomethyl, 2-methylthioethyl, 2-ethylthioethyl, 2-butylthioethyl, 2-hexylthioethyl, 3-methylthiopropyl, 3-ethylthiopropyl, 3-propylthiopropyl, 3-butylthiopropyl, 4-methylthiobutyl, 4-ethylthiobutyl, 4-propylthiobutyl, 4-butylthiobutyl, 6-methylthiohexyl, 6-ethylthiohexyl, 6-butylthiohexyl, 8-methylthiooctyl, 8-ethylthiooctyl and 8-butylthiooctyl.

Phenylalkyl means that the alkyl moiety is straight or branched chain alkyl having 1 to 8 carbon atoms and includes, for example, benzyl, 2-phenylethyl, 1-phenylethyl, 3-phenylpropyl, 4-phenylbutyl, 5-phenylpentyl, 6-phenylhexyl and 8-phenyloctyl.

Substituted phenylalkyl means above-mentioned phenylalkyl which is substituted by at least one substituent selected from the group consisting of halogen, amino, nitro, hydroxy, alkyl, alkoxy and haloalkyl on the phenyl nucleus.

Heteroarylalkyl means that the heteroaryl moiety is 5 to 10 membered mono- or fused-heteroaromatic ring having at least one heteroatom selected from the group consisting of nitrogen, oxygen and sulfur as mentioned above and the alkyl moiety is straight or branched chain alkyl having 1 to 8 carbon atoms and includes, for example, furfuryl, 3-furylmethyl, 2-thenyl, 3-thenyl, 2-, 3- or 4-pyridylmethyl, pyrazolylmethyl, 1-imidazolylmethyl, pyrimidinylmethyl, benzimidazolylmethyl, 2-(2-furyl)ethyl, 2-(2-thienyl)ethyl, 2-(2-pyridyl)ethyl, 2-(1-imidazolyl)ethyl, 3-(2-furyl)propyl, 3-(2-thienyl)propyl, 3-(2-pyridyl)propyl, 4-(2-furyl)butyl), 4-(2-thienyl)butyl and 4-(2-pyridyl)butyl.

Substituted heteroarylalkyl means that the substituted heteroaryl moiety is 5 to 10 membered mono- or fused-heteroaromatic ring which is substituted by at least one substituent selected from the group consisting of halogen, amino, nitro, hydroxy, alkyl, alkoxy and haloalkyl on the heteroaryl nucleus and which has at least one heteroatom selected from the group consisting of nitrogen, oxygen and sulfur as mentioned above, and that the alkyl moiety is straight or branched chain alkyl having 1 to 8 carbon atoms.

Cycloalkylalkyl means that the cycloalkyl moiety is cyclic alkyl having 3 to 7 carbon atoms and the alkyl moiety is straight or branched chain alkyl having 1 to 8 carbon atoms, and includes, for example, cyclopropylmethyl, cyclobutylmethyl, cyclopentylmethyl, cyclohexylmethyl, cycloheptylmethyl, 2-cyclopropylethyl, 2-cyclopentylethyl, 2-cyclohexylethyl, 3-cyclopropylpropyl, 3-cyclopentylpropyl, 3-cyclohexylpropyl, 4-cyclopropylbutyl, 4-cyclopentylbutyl, 4-cyclohexylbutyl, 6-cyclopropylhexyl and 6-cyclohexylhexyl.

The objective of the present invention is achieved by dissolving a racemic mixture of an aliphatic carboxylic acid in an inert solvent. Any solvent that is not reactive and dissolves substantially all of the mixture is acceptable. Thus, various aliphatic hydrocarbon solvents, i.e., hexane, heptane, octane, etc.; aromatic hydrocarbon solvents, i.e., benzene, toluene, xylene; and alcohol solvents, i.e., methanol, ethanol, 1-propyl alcohol, etc., are useful for such solvent. Mixtures of these solvents can also be used. Particularly preferred are the aliphatic hydrocarbon solvents, especially hexane.

The above solvent is employed to dissolve the reaction product of the racemic mixture of the aliphatic carboxylic acid and an achiral or racemic amine. The two materials react to form a carboxylate salt. However, by using the proper amine, a separable conglomerate results. The proper selection of the base is critical since the reaction product, the salt, must have the following properties:

i) the infrared spectrum of each of the enantiomeric salts, individually, and of the racemate salt are superposable;

ii) the melting point of each of the enantiomeric salts, individually, is greater than the melting point of the racemate salt; and iii) the solubility of each of the enantiomeric salts, individually, is less than the solubility of the racemate salt in the same solvent.

The organic bases used to provide the separable enantiomeric salts have the formula $R_mNH_n$, where m is an integer from 1 to 3, n is an integer from 0 to 2, and R is alkyl, phenyl, naphthyl, substituted phenyl, substituted naphthyl, alkenyl, alkynyl, cycloalkyl, heteroaryl, substituted heteroaryl, alkoxyalkyl, and alkylthioalkyl.

Preferably, the organic base is one where m is 1 and R is $C_1$ to $C_{12}$ alkyl, phenyl, $C_2$ to $C_6$ alkenyl, $C_2$ to $C_6$ alkynyl, $C_5$ to $C_8$ cycloalkyl, $C_5$ to $C_7$ heteroaryl, $C_1$ to $C_6$ alkoxyalkyl and $C_1$ to $C_6$ alkylthioalkyl.

Most preferably, the organic base is one where m is 1 and R is propyl, octyl, butyl and the like.

The aliphatic carboxylic acids of use in the present invention are those of the formula

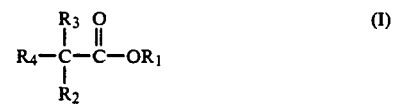

where $R_1$ is hydrogen or alkyl and $R_2$, $R_3$ and $R_4$ are independently different and are hydrogen, alkyl, cycloalkyl, alkenyl, alkynyl, phenyl, substituted phenyl, naphthyl, substituted naphthyl, heteroaryl, substituted heteroaryl, haloalkyl, alkoxyalkyl, alkylthioalkyl, phenylalkyl, substituted phenylalkyl, heteroalkylalkyl, substituted heteroalkylalkyl or cycloalkylalkyl.

Preferred compounds of formula I are those where $R_1$ is hydrogen or $C_1$ to $C_6$ linear or branched alkyl; $R_2$, $R_3$ and $R_4$ are independently different and are hydrogen or $C_1$ to $C_6$ linear or branched alkyl, e.g., methyl or ethyl; aralkyl, e.g., benzyl; cycloalkyl, e.g., cyclopropyl, cyclobutyl, cyclopentyl, cyclohexyl; alkyl substituted cycloalkyl, e.g., methylcyclohexyl; $C_6$ to $C_{10}$ aryl, e.g., phenyl unsubstituted or substituted with, for example, methyl, dimethyl, butyl especially isobutyl or phenyl substituted with $C_1$ to $C_4$ alkylthio, $C_1$ to $C_4$ alkoxy, cyano or halo, e.g., fluoro or chloro; $C_1$ to $C_6$ linear or branched alkoxy, e.g., phenoxy or phenoxy substituted with, for example, methyl, dimethyl, butyl or isobutyl or phenoxy substituted with $C_1$ to $C_4$ alkylthio, $C_1$ to $C_4$ alkoxy, cyano or halo; $C_1$ to $C_6$ alkylthio, e.g., methylthio; $C_2$ to $C_8$ cycloalkylthio; $C_6$ to $C_{10}$ arylthio; $C_6$ to $C_{10}$ arylcarbonyl, e.g., benzoyl; $C_4$ to $C_8$ cycloalkenyl, e.g., cyclohexenyl; trifluoromethyl; halo, e.g., fluoro or chloro; $C_4$ to $C_5$ heteroaryl, e.g., furyl, pyrrolyl, thienyl; or $C_{10}$ to $C_{14}$ aryl, e.g., naphthyl or naphthyl substituted with $C_1$ to $C_4$ alkyl, e.g., methyl; $C_1$ to $C_4$ alkoxy, e.g., ethoxy, halo; or biphenyl unsubstituted or substituted with methyl or halo, especially fluoro.

The most preferred compounds of formula I are those of the formula

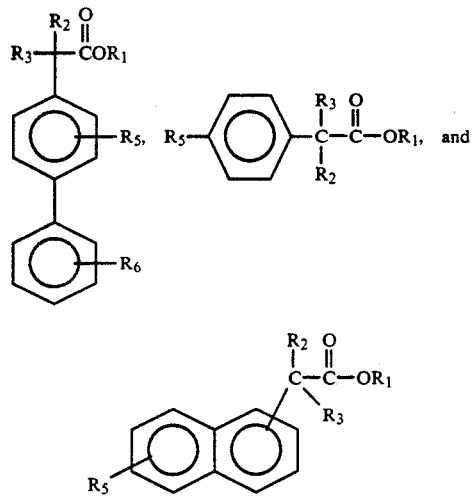

where $R_1$, $R_2$ and $R_3$ are as previously defined and $R_5$ and $R_6$ are $C_1$ to $C_4$ linear or branched alkyl, $C_1$ to $C_4$ linear or branched alkoxy or halo.

The improved process is particularly applicable to 2-(4-isobutylphenyl)propionic acid and especially in obtaining a preponderance of the S(+) isomer.

The process is carried out by using a supersaturated salt solution of a racemic mixture [a mixture of both the (+) and (−) or dextro and levo rotorary forms] or a mixture containing a preponderance of one of the enantiomers of these carboxylic acids, and seeding with the salt of the desired enantiomer. It should be understood that the process itself does not convert one form of the stereoisomers to the other form but only separates such forms from a racemic mixture. Pure salt is obtained by direct crystallization that requires a minimum number of recrystallizations (usually not more than two) to give an enantiomeric product with high optical purity.

The purified salt obtained from the process of the present invention may be further treated to produce the free aliphatic carboxylic acid thereof by using any conventional means. For example, hydrolysis of the salt with a dilute mineral acid and extraction with a suitable organic solvent produces the purified aliphatic carboxylic acid. Further extraction and recrystallization with a suitable solvent can increase the purity to even greater extent. Thus, the optically pure acid is obtained by resolution without using an optically active amine.

It should be noted that the process of the present invention is particularly adapted to the economical conversion of racemic mixtures to the enantiomeric S- or (+)- component. (Of course, the R-component may be the desired one, in which case the following discussion should be applied in reverse). The method of the present invention essentially provides a solid precipitate enriched in the S-enantiomer. Liberation of the desired carboxylic acid S-enantiomer from the precipitated salt is readily accomplished by acidification of the salt with, for example, dilute mineral acid or any other inorganic or organic acid conventionally known to hydrolyze salts of this nature.

EXAMPLES

The following examples are given to illustrate the invention and are not intended as any limitation thereof.

General

Optical purity determinations of ibuprofen were made by HPLC using a chiral AGP ($\alpha$-glycoprotein) column. The salts were prepared by treating a solution of ibuprofen in diethyl ether, hexane, or petroleum ether with the amine solution and isolating the precipitate by filtration.

EXAMPLE 1

Resolution of Octylamine salt

Ibuprofen of 58% S optical purity (12 g; 58 mmol) was dissolved in 250 mL of hexane at 50°–60° C. n-Octylamine (7.5 g; 58 mmol) was added and about 100 mL of solvent was removed by evaporation. The solution was cooled to 30° C. and seeded with a few mg of optically pure S(+)-ibuprofen salt and stirred. The precipitate was filtered and washed with petroleum ether to give 4.4 g of 85% S-ibuprofen-octylamine salt. This salt was recrystallized in 25 mL of hexane, seeding again with pure S-ibuprofen salt. 1.4 g of ibuprofen salt with an enantiomeric purity of 97% S was recovered.

EXAMPLE 2

Resolution of Isopropylamine Salt

Isopropylamine salt of 62% S-ibuprofen (6.8 g) was dissolved in 100 mL of isopropanol at about 50° C. The solution was cooled to 38° C., seeded with 5 mg of pure S-ibuprofen salt and stirred for 45 minutes. The precipitated solid was isolated by filtration to obtain the salt of 90% S-ibuprofen; yield =2.6 g.

EXAMPLE 3

Resolution of n-Amylamine Salt

One gram of the n-amylamine salt of 59% S-ibuprofen was dissolved in 20 mL of hexane at about 50° C. and then cooled to 0°–5° C. The solution was seeded with a few mg of pure S-ibuprofen salt and stirred for 30 minutes. The precipitated solid was isolated by filtration to obtain 0.3 g of the salt of 88% S-ibuprofen.

EXAMPLE 4

Resolution of n-Propylamine Salt a) One gram of the n-propylamine salt of 65% S-ibuprofen was dissolved in 50 mL of hexane at 55° C. The solution was cooled to 35° C., seeded with 5 mg of pure S-ibuprofen-propylamine salt and left to crystallize for 30 minutes. By filtering the precipitate, 0.38 g of 80% S-ibuprofen salt was recovered.

b) The propylamine amine salt of 63% S-ibuprofen (3.4 g) was dissolved in hexane at 60° C. The solution was cooled to 45°–50° C., seeded with 9 mg of pure S-ibuprofen salt and stirred at 35° C. The crystallized salt was filtered to isolate 1.4 g of 87% S-ibuprofen salt.

EXAMPLE 5

Resolution of t-Butylamine Salt

The t-butylamine salt of 63% S-ibuprofen (370 mg) was dissolved in 35 mL of isopropanol and 10 mL of methanol at 50° C. The solution was cooled to 25° C., seeded with 3 mg of pure S-ibuprofen salt stirred and filtered. 20 mg of 94% S-ibuprofen salt was recovered.

EXAMPLE 6

Resolution of Racemic α-Methylbenzylamine Salt

A supersaturated solution was obtained by dissolving 4.5 g of R,S-α-methylbenzylamine salt of racemic ibuprofen and 0.5 g S-ibuprofen salt in 60 mL of isopropanol at 70° C. and cooling the solution to 40° C. The solution was seeded with 16 mg of pure S-ibuprofen salt and stirred at 30° C. The precipitate was filtered and washed with 10 mL of acetone and 30 mL of ether to recover 2.6 g of 62% S-ibuprofen salt. A 2.2 g sample of this salt was recrystallized by dissolving in 30 mL of hot isopropanol and cooling to room temperature. 1.3 g of 74% S-ibuprofen was isolated.

The amine portion of the recrystallized salt was liberated and it was surprisingly found to be optically active (68% S) by polarimetry. Interestingly, the resolution of ibuprofen resulted in the co-resolution of the racemic α-methylbenzylamine.

We claim:

1. A process for separating the enantiomers of a racemic mixture of an aliphatic carboxylic acid or ester thereof having the formula:

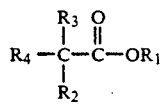
(I)

where $R_1$ is hydrogen or alkyl; $R_2$, $R_3$ and $R_4$ are independently different and are hydrogen; alkyl; cycloalkyl; alkenyl; alkynyl; phenyl; naphthyl; phenyl or naphthyl substituted by at least one substituent selected from the group consisting of halogen, amino, nitro, hydroxy, alkyl, alkoxy and haloalkyl; heteroaryl; heteroaryl substituted by at least one substituent selected from the group consisting of halogen, amino, nitro, hydroxy, alkyl, alkoxy and haloalkyl; alkoxyalkyl; alkylthioalkyl; phenylalkyl; phenylalkyl substituted with at least one substituent selected from the group consisting of halogen, amino, nitro, hydroxy, alkyl, alkoxy and haloalkyl; heteroarylalkyl; heteroarylaklyl substituted by at least one substituent selected from the group consisting of halogen, amino, nitro, hydroxy, alkyl, alkoxy and haloalkyl; or cycloalkylalkyl, comprising forming a supersaturated solution of a conglomerate salt of said racemic mixture by reaction with a base, said conglomerate salt being a mixture of the enantiomeric salts and having the following properties:

i) the infrared spectrum of each of the enantiomeric salts, individually, and of the racemate salt are superposable;

ii) the melting point of each of the enantiomeric salts, individually, is greater than the melting point of the racemate salt; and iii) the solubility of each of the enantiomeric salts, individually, is less than the solubility of the racemate salt in the same solvent;

and precipitating the enantiomeric salt from the supersaturated solution.

2. The process according to claim 1 wherein said base is an achiral or racemic amine and has the formula $R_mNH_n$, where m is an integer from 1 to 3, n is an integer from 0 to 2, and R is alkyl, phenyl, naphthyl, phenyl or naphthyl substituted by at least one substituent selected from the group consisting of halogen, amino, nitro, hydroxy, alkyl, alkoxy and haloalkyl, heteroaryl, alkenyl, alkynyl, cycloalkyl, heteroarylalkyl, heteroarylalkyl substituted by at least one substituent selected from the group consisting of halogen, amino, nitro, hydroxy, alkyl, alkoxy and haloalkyl, alkoxyalkyl, or alkylthioalkyl.

3. A process for separating the enantiomers of a racemic mixture of an aliphatic carboxylic acid or ester thereof having the formula:

(I)

where $R_1$ is hydrogen or $C_1$ to $C_6$ linear or branched alkyl; $R_2$, $R_3$ and $R_4$ are independently different and are hydrogen or $C_1$ to $C_6$ linear or branched alkyl; aralkyl; cycloalkyl; alkyl substituted cycloalkyl; phenyl unsubstituted or substituted with methyl, dimethyl, butyl, isobutyl, $C_1$ to $C_4$ alkylthio, $C_1$ to $C_4$ alkoxy, cyano or halo; $C_1$ to $C_6$ linear or branched alkoxy; phenoxy or phenoxy substituted with methyl, dimethyl, butyl, isobutyl, $C_1$ to $C_4$ alkylthio, $C_1$ to $C_4$ alkoxy, cyano or halo; $C_1$ to $C_6$ alkylthio; $C_2$ to $C_8$ cycloalkylthio; $C_6$ to $C_{10}$ arylthio; $C_6$ to $C_{10}$ arylcarbonyl; $C_4$ to $C_8$ cycloalkenyl; trifluoromethyl; halo; $C_4$ to $C_5$ heteroaryl; naphthyl or naphthyl substituted with $C_1$ $C_4$ alkyl, $C_1$ to $C_4$ alkoxy, or halo; or biphenyl unsubstituted or substituted with methyl or halo; comprising forming a supersaturated solution of a conglomerate salt of said racemic mixture by reaction with a base, said conglomerate salt being a mixture of the enantiomeric salts and having the following properties:

i) the infrared spectrum of each of the enantiomeric salts, individually, and of the racemate salt are superposable;

ii) the melting point of each of the enantiomeric salts, individually, is greater than the melting point of the racemate salt; and iii) the solubility of each of the enantiomeric salts, individually, is less than the solubility of the racemate salt in the same solvent;

and precipitating the enantiomeric salt from the supersaturated solution.

4. The process according to claim 3 wherein the reaction of said racemic mixture and said base is carried out in a solvent.

5. The process according to claim 4 wherein said solvent is an aromatic hydrocarbon, an aliphatic hydrocarbon, an aliphatic alcohol or mixtures thereof.

6. The process according to claim 5 wherein said solvent is benzene, toluene, xylene, methanol, ethanol or 1-propanol.

7. The process according to claim 6 wherein said solvent is hexane.

8. A process for separating the enantiomers of 2-(4-isobutylphenyl)propionic acid from a racemic mixture, comprising forming a supersaturated solution of a conglomerate salt of said racemic mixture by reaction with a base, said conglomerate salt being a mixture of the enantiomeric salts and having the following properties:
  i) the infrared spectrum of each of the enantiomeric salts, individually, and of the racemate salt are superposable;
  ii) the melting point of each of the enantiomeric salts, individually, is greater than the melting point of the racemate salt; and
  iii) the solubility of each of the enantiomeric salts, individually, is less than the solubility of the racemate salt in the same solvent;
and precipitating the enantiomeric salt from said supersaturated solution.

9. A process for separating the enantiomers of a racemic mixture of an aliphatic carboxylic acid or ester thereof having the formula:

$$R_4-\underset{\underset{R_2}{|}}{\overset{\overset{R_3}{|}}{C}}-\overset{\overset{O}{\|}}{C}-OR_1 \qquad (I)$$

hydrogen or $C_1$ to $C_6$ linear or branched alkyl, $R_2$ $R_3$ and $R_4$ are independently methyl; ethyl; benzyl; cyclopropyl; cyclobutyl; cyclopentyl; cyclohexyl; methylcyclohexyl; phenyl substituted with fluoro or chloro; phenoxy substituted with fluoro or chloro; methylthio; benzoyl; cyclohexenyl; trifluoromethyl; fluoro; chloro; furyl; pyrrolyl; thienyl; naphthyl substituted with methyl, methoxy or ethoxy; or biphenyl substituted with fluoro; comprising forming a supersaturated solution of a conglomerate salt of said racemic mixture by reaction with a base, said conglomerate salt being a mixture of the enantiomeric salts and having the following properties:
  i) the infrared spectrum of each of the enantiomeric salts, individually, and of the racemate salt are superposable;
  ii) the melting point of each of the enantiomeric salts, individually, is greater than the melting point of the racemate salt; and
  iii) the solubility of each of the enantiomeric salts, individually, is less than the solubility of the racemate salt in the same solvent;
and precipitating the enantiomeric salt from the supersaturated solution.

10. A process for separating the enantiomers of a racemic mixture of a compound selected from the group having the formula:

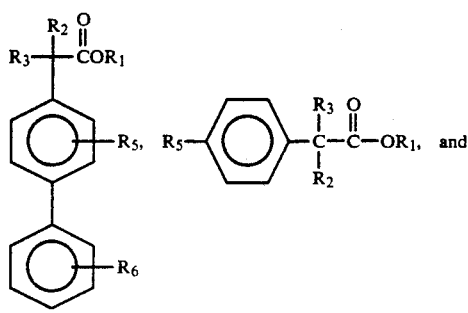

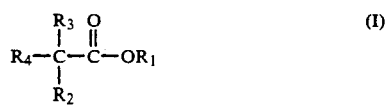

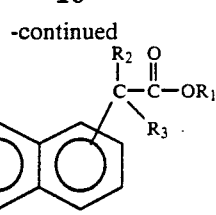

where $R_1$ is hydrogen or $C_1$ to $C_6$ linear or branched alkyl; $R_2$ and $R_3$ are independently different and are hydrogen; methyl or ethyl; benzyl; cyclopropyl, cyclobutyl, cyclopentyl, or cyclohexyl; methylcyclohexyl; phenyl unsubstituted or substituted with, methyl, dimethyl, butyl, isobutyl, $C_1$ to $C_4$ alkylthio, $C_1$ to $C_4$ alkoxy, cyano, fluoro or chloro; phenoxy or phenoxy substituted with methyl, dimethyl, butyl, isobutyl, $C_1$ to $C_4$ alkylthio, $C_1$ to $C_4$ alkoxy, cyano or halo; methylthio; $C_2$ to $C_8$ cycloalkylthio; $C_6$ to $C_{10}$ arylthio; benzoyl; cyclohexenyl; trifluoromethyl; fluoro or chloro; furyl; pyrrolyl; thienyl; naphthyl or naphthyl substituted with methyl, ethoxy, or halo; or biphenyl unsubstituted or substituted with methyl or fluoro; and $R_5$ and $R_6$ are $C_1$ to $C_4$ linear or branched alkyl, $C_1$ to $C_4$ linear or branched alkoxy or halo; comprising forming a supersaturated solution of a conglomerate salt of said racemic mixture by reaction with a base, said conglomerate salt being a mixture of the enantiomeric salts and having the following properties:
  i) the infrared spectrum of each of the enantiomeric salts, individually,, and of the racemate salt are superposable;
  ii) the melting point of each of the enantiomeric salts, individually, is greater than the melting point of the racemate salt; and
  iii) the solubility of each of the enantiomeric salts, individually, is less than the solubility of the racemate salt in the same solvent;
and precipitating the enantiomeric salt from the supersaturated solution.

11. A process for separating the enantiomers of 2-(4-isobutylphenyl)propionic acid from a racemic mixture, comprising forming a supersaturated solution of a conglomerate salt of said racemic mixture by reaction with an achiral or racemic amine having the formula $R_mNH_n$, where m is an integer from 1 to 3, n is an integer from 0 to 2, and R is alkyl, phenyl, naphthyl, substituted phenyl, substituted naphthyl, alkenyl, alkynyl, cycloalkyl, heteroaryl, substituted heteroaryl, alkoxyalkyl, or alkylthioalkyl, said conglomerate salt being a mixture of the enantiomeric salts and having the following properties:
  i) the infrared spectrum of each of the enantiomeric salts, individually, and of the racemate salt are superposable;
  ii) the melting point of each of the enantiomeric salts, individually, is greater than the melting point of the racemate salt; and
  iii) the solubility of each of the enantiomeric salts, individually, is less than the solubility of the racemate salt in the same solvent;
and precipitating the enantiomeric salt from said supersaturated solution.

12. The process according to claim 11 where m is 1 and R is $C_1$ to $C_{12}$ alkyl, phenyl, $C_2$ to $C_6$ alkenyl, $C_2$ to $C_6$ alkynyl, $C_5$ to $C_8$ cycloalkyl, $C_5$ to $C_7$ heteroaryl, $C_1$ to $C_6$ alkoxyalkyl or $C_1$ to $C_6$ alkylthioalkyl.

13. The process according to claim 12 where m is 1 and R is propyl, octyl or butyl.

* * * * *